(12) United States Patent
Lee (10) Patent No.: US 11,318,219 B1
(45) Date of Patent: May 3, 2022

(54) VOLCANIC ROCK FLUID DIFFUSER

(71) Applicant: BLOOMY LOTUS LIMITED, Hong Kong (HK)

(72) Inventor: Leander Lee, New York, NY (US)

(73) Assignee: BLOOMY LOTUS LIMITED, Hong Kong (HK)

( * ) Notice: Subject to any disclaimer, the term of this patent is extended or adjusted under 35 U.S.C. 154(b) by 0 days.

(21) Appl. No.: 17/090,132

(22) Filed: Nov. 5, 2020

(51) Int. Cl.
*A61L 9/03* (2006.01)

(52) U.S. Cl.
CPC ............ *A61L 9/03* (2013.01); *A61L 2209/14* (2013.01)

(58) Field of Classification Search
CPC ..... A61L 9/00; A61L 9/02; A61L 9/03; A61L 9/032; A61L 9/04; A61L 9/044; A61L 9/12; A61L 9/122; A61L 2209/13; A61L 2209/14
See application file for complete search history.

(56) References Cited

U.S. PATENT DOCUMENTS

| 8,900,518 | B2 * | 12/2014 | Seck | ........................ | A61L 9/205 |
| | | | | | 422/121 |
| 2018/0099065 | A1 * | 4/2018 | Burns | ...................... | A61L 9/044 |
| 2019/0022270 | A1 | 1/2019 | Yang | | |

FOREIGN PATENT DOCUMENTS

JP 2010046411 A 3/2010

OTHER PUBLICATIONS

Black Ice Patch. (n.d.). Activated Charcoal Filter for the Breathing Mask. Retrieved Nov. 6, 2020, from https://blackicepatch.com/products/activated-charcoal-filter.
InvisiClean Personal Mini Air Purifier. (n.d.). Retrieved Nov. 6, 2020, from https://www.invisiclean.com/invisiclean-personal-mini-air-purifier.html.
Negative Ion Aroma Essential Oil Diffuser Ultrasonic Air Humidifier 500ml. (n.d.). Retrieved Nov. 6, 2020, from https://negative-ion-store.myshopify.com/products/negative-ion-aroma-essential-oil-diffuser-ultrasonic-air-humidifier-500ml.
Concrete Lava Rock Diffusers. (2019). Retrieved on Nov. 6, 2020 at https://media.doterra.com/us/en/pips/concrete-lava-rock-diffusers.pdf.

* cited by examiner

*Primary Examiner* — Timothy C Cleveland
(74) *Attorney, Agent, or Firm* — Hamre, Schumann, Mueller & Larson, P.C.

(57) ABSTRACT

A fluid diffuser system includes volcanic rock material positioned in a receptacle or within a gas-permeable filter. Airflow can be driven through the diffuser system, such as through the filter, to add droplets or vapors of fluids (e.g., aromatic fluids such as essential oils) to the airflow and then into the surrounding atmosphere of the system. The rock material can be highly porous to retain fluids in a natural, environmentally-friendly, and sustainable manner. Some systems are wearable and can use movement of the system to drive air past the rock material, and some systems can employ an air mover (e.g., fan) to drive airflow.

16 Claims, 7 Drawing Sheets

VOLCANIC ROCK FLUID DIFFUSER

TECHNICAL FIELD

The present disclosure relates to the field of fluid diffusers, and more particularly to a diffuser using a volcanic rock material for holding fluid to be diffused.

BACKGROUND

In daily life, essential oils and other therapeutic or aromatic fluids are often used to improve the surrounding environment or to perform medical treatment, such as sterilization, disinfection or changing environmental odor, etc. When using these fluids, an atomizer or diffuser is often operated to atomize, evaporate, or otherwise break into droplets the essential oils for facilitating diffusion of the essential oils into the environment.

SUMMARY

One aspect of the present disclosure relates to a liquid diffuser comprising a housing shell having an inlet and an outlet and a filter assembly positioned in the housing shell. The filter assembly can include a first retainer layer, a second retainer layer, and an absorbent material supply positioned between the first and second retainer layers. The diffuser can also include an air mover positioned in the housing shell and configured to draw air through the filter assembly as the air passes from the inlet to the outlet.

In some embodiments, the absorbent material supply can comprise a plurality of volcanic rocks. The filter assembly can be positioned between the inlet and the air mover. In some embodiments, airflow can be configured to enter the inlet along a first direction and can be configured to exit the outlet along a second direction, with the first direction being perpendicular to the second direction. When the diffuser is in an upright operational position, airflow can be configured to pass through the absorbent material supply along a gravitational direction. In some embodiments, the diffuser can further comprise a fluid tank positioned below the filter assembly. The housing can also comprise a funnel surface at the inlet, with the funnel surface comprising a bottom opening directed toward the filter assembly.

Another aspect of the disclosure relates to a filter for a liquid diffuser that comprises a first filter layer having a first fluid-penetrable material, a porous volcanic rock layer adjacent to the first filter layer, a second filter layer having a second fluid-penetrable material adjacent to the volcanic rock layer, and a binder coupling the first filter layer, the porous volcanic rock layer, and the second layer in a layered orientation around a perimeter of the porous volcanic rock layer.

In some configurations, the porous volcanic rock layer can comprise an aggregate of porous volcanic rock particles. In some embodiments, a first portion of the aggregate overlaps a second portion of the aggregate along an axis extending through a vertical dimension of the filter. The first and second fluid-penetrable materials can comprise antibacterial materials. The binder can be configured to clamp the first and second filter layers toward each other. The binder can be adhered to the perimeter of the porous volcanic rock layer. In some cases, the filter can also comprise a shell having a fluid reservoir positioned underneath the porous volcanic rock layer.

Yet another aspect of the disclosure relates to a lava rock fluid diffuser comprising a housing defining an air inlet and an air outlet, a fluid flow path extending from the air inlet to the air outlet of the housing, and a lava rock material positioned in the housing, with the lava rock material having a recessed surface configured to retain a fluid. In the diffuser, evaporation of the fluid from the lava rock material can move the fluid into the fluid flow path to exit the outlet of the housing.

In some embodiments, the lava rock material can be positioned within a filter that is positioned in the fluid flow path and filters air passing between the air inlet and the air outlet. A liquid reservoir can be positioned spaced below the lava rock material. The fluid flow path can change directions between the air inlet and the air outlet. In some embodiments, the diffuser comprises a negative ion generator positioned in the housing and configured to emit negative ions into the fluid flow path. In some embodiments, the lava rock material is positioned on a tray, and the tray is removable from the housing through a side surface of the housing.

The above summary of the present invention is not intended to describe each embodiment or every implementation of the present invention. The figures and the detailed description that follow more particularly exemplify one or more preferred embodiments.

BRIEF DESCRIPTION OF THE DRAWINGS

The accompanying drawings and figures illustrate a number of exemplary embodiments and are part of the specification. Together with the present description, these drawings demonstrate and explain various principles of this disclosure. A further understanding of the nature and advantages of the present invention may be realized by reference to the following drawings. In the appended figures, similar components or features may have the same reference label.

While the embodiments described herein are susceptible to various modifications and alternative forms, specific embodiments have been shown by way of example in the drawings and will be described in detail herein. However, the exemplary embodiments described herein are not intended to be limited to the particular forms disclosed. Rather, the instant disclosure covers all modifications, equivalents, and alternatives falling within the scope of the appended claims.

DETAILED DESCRIPTION

Conventional air purifiers are used to sterilize or filter air passing through them using a negative ions and/or filtering functions. Often, filters and aroma diffusers in these devices are two different parts, and consumers must therefore inconveniently clean or replace the filter and the aroma emission materials separately. In some embodiments of the present disclosure, a filter is provided with aromatic oil absorbing material such as volcanic rock particles or pebbles, or a slab, and the filter can remove particles or contaminants from airflow through a diffuser, purifier, or atomizer while the same airflow is infused with diffused aromatic fluid particles that evaporate or are otherwise swept away from the crevices, pores, and surfaces of the volcanic rock supply. With this configuration, a user can simultaneously and conveniently replace or clean the filter and the liquid aroma emission material by removing or cleaning a single combined part.

A filter of the present disclosure can comprise a layered construction wherein a rock layer is positioned between filter or retainer material layers. For example, aggregate lava rock or other volcanic rock can be arranged in a substantially planar configuration between two substantially planar layers of filter material (e.g., cotton, spun fiberglass, paper, cloth, other fibrous material, or other fluid-penetrable material). As used herein, a fluid-penetrable material permits liquids applied to one side thereof to pass through to the other side thereof. Essential oil or other aromatic liquid can be deposited on the outside of one of the filter material layers, and the liquid can penetrate and flow through the filter material layer. The liquid can then fall or seep into the middle rock layer which, due to its abundant pores, crevices, and voids, can absorb and retain a substantial amount of oil in the filter. The depth of the pores, crevices, and voids can help prolong the duration of time that the liquid evaporates from the aggregate layer since the liquid evaporates from the surfaces of the pores while small reservoirs of the liquid are protected from quick evaporation within the pores, crevices, and voids. Furthermore, any liquid that passes through the aggregate layer can be absorbed and filtered by the second layer of filter material. In some embodiments, a cup or tank is also positioned beneath the second filter layer to catch any drops that penetrate entirely through the internal filter layers.

An air mover (e.g., a fan, impeller, rotor, vacuum, pump, or other airflow generator) can draw air through the filter to strain particles from the air by causing the particles to be lodged in layers of filter material and to simultaneously imbue the air with particles of the aromatic liquid by drawing evaporated or atomized liquid droplets from the filter material and from the surfaces of liquid repositories on the aggregate rocks within the filter. The air mover can then drive the filtered and aroma-imbued air out of the diffuser (e.g., into the surrounding environment of a diffuser housing holding the filter). In some embodiments, the diffuser can further comprise negative ion purifier capability, wherein negative ions can be dispersed into the airstream that moves through the diffuser. A negative ion generator can be positioned in the device and can generate negative ions that are supplied to the airstream emitted from the device to remove particles in the path of the airstream that are external to the device.

In some arrangements, a diffuser is provided wherein volcanic rock material is located in the device in a position where airflow through the diffuser is configured to pass through, around, or over the aggregate material. For example, the rock material can be positioned in the diffuser in a box, tray, or other vented, airway-exposed, or open-air receptacle inside the diffuser housing rather than being part of, or in contact with, a filter or layer of filter material. Aromatic liquid can be applied to and absorbed by the rock material within the diffuser, and airflow through the diffuser can pass by or over the rock material to carry and waft away droplets of the fluid evaporated or atomized from the surface of the rock material. In some embodiments, the container for tray or the rock material can be configured to be removable from a larger housing of the device so that the aggregate material can be more easily accessed for application/renewal of oil, removed and exchanged for other rock material, or cleaned independent of the rest of the housing.

A conventional essential oil diffuser, atomizer, or nebulizer device typically generates airflow to extract a fluid (e.g., essential oil) from a bottle and to transfer the fluid out of the device into the surrounding atmosphere. However, these actions can cause inefficiently large-sized droplets of fluid to pass into the airstream, so the diffusion or atomization performance of the device is poor and oil is not well-distributed. The large fluid droplets can be wasted while only diffusing over short distances (e.g., falling nearby the diffuser device rather than spreading throughout the air in the vicinity of the device). To reduce the waste of these fluids, a filter is often used for filtering the atomized airflow mixed with the fluid droplets so as to recycle the fluid droplets. However, filters can be overly effective, wherein droplets passing from one side of the filter are completely prevented from reaching the other side, thereby preventing any fluids from being diffused into the outflow of air. Additionally, users of the diffuser devices are health-conscious and often prefer natural remedies, but the filters used in the devices are often made with artificial plastics, fibers, and similar materials. Accordingly, some embodiments of the present disclosure relate to using natural volcanic rock material as part of a filter that comprises more natural substances and that is configured to permit certain fluid droplets to pass through or be emitted from the filter into the outflow of air. In some embodiments, large droplets of fluids can be collected in a tank or reservoir by the filter or a housing of the filter in a manner that prevents large amounts of fluid from being wastefully emitted from the device without proper diffusion. Furthermore, filters of the present disclosure can comprise fine fibers configured to re-atomize large droplets as a pressure difference between the outer sides of the filter force airflow through and between the fibers where the fluid may otherwise collect and stagnate.

Unless specified otherwise, it should be understood that, “length”, “width”, “upper”, “lower”, “front”, “back”, “left” and “right”, “vertical”, “horizontal”, “top”, “bottom”, “inside”, “outside” and other terms indicating the orientation or positional relationship are used to refer to orientation or positional relationship shown in the drawings, only for the purpose of facilitating and simplifying the description of the invention, instead of indicating or implying that the indicated device or component must have a specific orientation and constructed and operated in a particular orientation, and therefore cannot be construed as limiting.

In the description of the present invention, it should be noted that the terms “install,” “connected,” and “connect” should be interpreted broadly unless specifically defined or limited otherwise. For example, the components may be fixedly connected, detachably connected, or integrally connected. The connection can be mechanical or electrical. The connection can be direct or indirect (connected through an intermediary). It can also be the internal communication of two components or the interaction between two components. Those of ordinary skill in the art can understand the specific meanings of the above terms in the present disclosure according to specific circumstances.

The present description provides examples, and is not limiting of the scope, applicability, or configuration set forth in the claims. Thus, it will be understood that changes may be made in the function and arrangement of elements discussed without departing from the spirit and scope of the disclosure, and various embodiments may omit, substitute, or add other procedures or components as appropriate. For instance, the methods described may be performed in an order different from that described, and various steps may be added, omitted, or combined. Also, features described with respect to certain embodiments may be combined in other embodiments.

Figure 1:
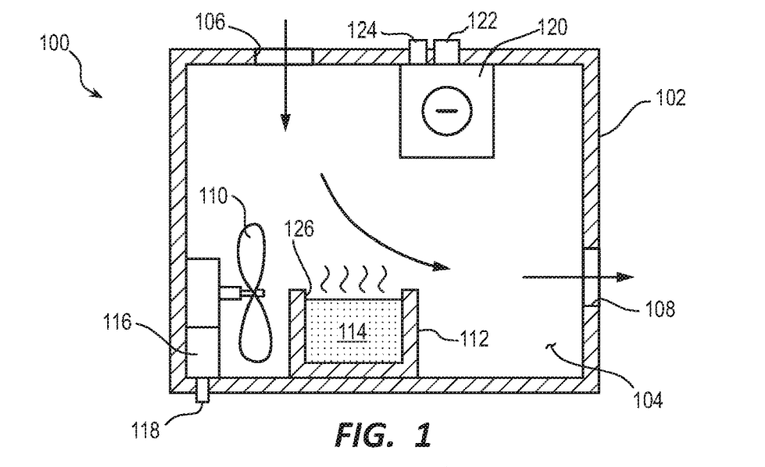
FIG. 1 is a side section view diagram of a diffuser system of the present disclosure.

FIG. 1 is a schematic section view illustration of a diffuser system 100 of an embodiment of the present disclosure. The diffuser system 100 can comprise a housing 102 defining an internal chamber 104 connected to a first opening 106 and a second opening 108. The internal chamber 104 can contain an air mover 110 (e.g., a fan, impeller, rotor, vacuum, pump, or other airflow generator) configured to generate airflow through the internal chamber 104, wherein air is drawn into one of the openings 106, 108 and out the other opening. In this embodiment, airflow is illustrated entering the internal chamber 104 via the first opening 106 (i.e., the first opening 106 can function as an inlet) and exiting the internal chamber 104 via the second opening 108 (i.e., the second opening 108 can function as an outlet). The internal chamber 104 can contain a receptacle 112 configured to contain a supply of substantially absorbent rock 114 or other absorbent material (e.g., cotton, polyethylene foam, or other porous and liquid-absorbent material). Aromatic fluids such as essential oils can be deposited on the rock supply 114 (e.g., through one of the openings 106, 108, and fluids can coat the rock supply 114 and/or fill voids in the surfaces of the rocks or in between individual stones or grains in the rock supply 114. The fluids can naturally evaporate from the rock supply 114 into the internal chamber 104, thereby causing vapors and droplets of the fluids to float into the airflow generated by the air mover 110. As the airflow moves through the diffuser system 100, the fresh inlet air (e.g., from opening 106) can sweep the vapor or droplets through the internal chamber 104 and then out of the housing 102 (e.g., through opening 108). The air surrounding the housing 102 can thereby contain aromatic fluids dispersed by action of the system 100.

In addition, the system 100 can comprise a power source (e.g., a battery 116) and a control device (e.g., a switch 118) whereby the air mover 110 can be powered and controlled. In some embodiments, the system 100 can also include a negative ion generator 120 configured to emit ions into the internal chamber 104 which are swept out of the housing 102 by the airflow. The negative ion generator 120 can emit negative ions directly out of the housing 102 (e.g., through a separate ion generator outlet tube 122), and the negative ions can be diffused into the surrounding environment of the system 100 separately from the airflow that contains the diffused fluids from the rock supply 114. The negative ion generator 120 can be electrically powered by the power source (e.g., battery 116) and controlled by one or more switches or other electronic control features of the system 100 (e.g., 118). In some embodiments, the negative ion generator 120 can draw air from the internal chamber 104 to infuse with negative ions. In other cases, the generator 120 can receive air that is external to the housing 102 (e.g., through an inlet tube 124 or vent).

The housing 102 is shown schematically in FIG. 1 as having a substantially single body construction. In some cases, the housing 102 can comprise multiple sections or parts, such as a "clamshell" housing having two or more housing portions that are reversibly attachable to each other in order to allow a user to take apart the housing 102 for access the internal chamber 104 (e.g., to add fluids to the rock supply 114) and also to allow the user to reassemble the housing 102. The housing 102 can thereby protect the internal components from damage or debris and make the system 100 more safely portable.

The first and second openings 106, 108 can each comprise a single opening or multiple openings (e.g., slits or holes in the housing 102) that enable airflow to pass from an exterior of the housing 102 to the internal chamber 104. The first opening 106 can beneficially be positioned on top of the housing 102 to allow a user more direct access to the top of the rock supply 114 through the first opening 106. In some embodiments, the first opening 106 can be on a different side or bottom surface of the housing 102. Similarly, the second opening 108 can be positioned on a side, top, or bottom surface of the housing 102. In some cases, a user can directly access the rock supply 114 via the second opening 108, such as to apply oil to the rock supply 114. In some embodiments, additional openings can be included in the housing 102, such as openings for inlet and outlet airflow for the negative ion generator 120 or for installing or removing the receptacle 112, battery 116, or air mover 110. The openings 106, 108 can define respective inlet and outlet directions of airflow, and those directions can be perpendicular to each other, as illustrated in FIG. 1. When the airflow is configured to change directions through the housing 102, the airflow speed can be reduced so as to control (e.g., reduce) the rate of convective whisking away of vapors from fluids within the housing 102.

The air mover 110 can be an electrical component configured to be powered by an electrical power source (e.g., battery 116 or a connection to an electrical utility grid, solar generator, etc.). In some cases, the air mover 110 can be mechanically driven, such as by a crank extending from the housing 102 that drives rotation of fan blades in the internal chamber 104. Additionally, in some cases, the air mover 110 can comprise an air compressor and/or a supply of compressed air that is configured to dispense a burst of air into the internal chamber 104 that drives airflow over the rock supply 114 and out of at least one of the openings 106, 108. The rate of airflow generated by the air mover 110 can be controllable by a controller (e.g., a printed circuit board or other type of connected electronic controller) to make the air mover 110 blow air with more or less volume displacement (e.g., cubic feet per minute (CFM)) or, in some cases, to reverse or otherwise change the direction of airflow through the internal chamber 104.

The receptacle 112 can define an internal container for a rock supply 114 and/or aromatic fluids that are deposited in the receptacle 112 with the rock supply 114. The receptacle 112 can be integrally formed with or attached to the interior of the housing 102. In some embodiments, the receptacle 112 can be removable or at least movable relative to the housing 102 to allow a user to move the rock supply 114 and/or gain access to the internal container area of the receptacle 112 to change the rock supply, to clean the receptacle 112, to swap out fluids, to perform similar actions, and combinations thereof. See also FIGS. 9-11.

In some configurations, the receptacle 112 can have a single open side from which evaporated or otherwise diffused fluid can exit the receptacle 112. For example, as shown in FIG. 1, the top of the receptacle 112 comprises an opening 126, and the sides and bottom of the receptacle 112 are fluid-tight prevent leakage or spilling of fluids or rocks deposited in the receptacle 112. The opening 126 can include a single large opening, as shown in FIG. 1, or can include a plurality of holes or slots sized and configured to prevent rocks of the rock supply 114 from falling out of the receptacle 112 while allowing vapor and small droplets of fluid to pass into the internal chamber 104 external to the receptacle 112. Furthermore, in some cases, the receptacle 112 can comprise multiple sides with openings in order to provide various rates of airflow or fluid evaporation from the receptacle 112.

The rock supply 114 can comprise a variety of different types of rock or stone pieces held within the receptacle 112. In example embodiments, the rock supply 114 can comprise volcanic rocks, lava rocks, igneous rocks, porous rocks, materials having high porosity/pockets/recesses (i.e., absorbent rocks, sponge, or polymer foam), similar rock materials, synthetic or simulated lava rock, and combinations thereof. Thus, as described herein, a "rock supply" includes rigid materials having high porosity and related surface features similar to volcanic rocks. Rocks (or the other above-listed materials) of this nature can beneficially absorb and/or hold fluid on their surfaces due to naturally-occurring surface formations including, for example, recesses, pockets, craters, cracks, and similar features that can act as small reservoirs or chambers within which fluids can collect when fluids are poured or dropped onto those formations. For example, in some embodiments, fluids can be deposited onto the rock supply 114 that pass into the surface formations, thereby affecting the amount of surface area of the fluid that is exposed to the air due to the internal wall surfaces of the surface formations containing the fluid similar to open-mouth cavities or bottles. Volcanic rocks can also desirably retain heat and emit infrared radiation for improved user comfort and mild heating capability. In some embodiments, a heating element can be used to heat a rock supply so that the liquid on the rock supply can evaporate more quickly or so that the rock supply can diffuse heat into air passing through or across its surface.

As compared to a simple pool of liquid, the rock supply 114 can change the effective vaporization duration of a predetermined amount of liquid by limiting or increasing the amount of liquid surface area from which evaporation can take place. In other words, a simple shallow pool of liquid may have more surface area for evaporation than the collective surface areas of many small pores holding the same amount of liquid in the rock supply 114, so the rock-supported liquid can evaporate more slowly than the pool. Additionally, with larger quantities of liquid, the larger amount of liquid, when held by the rock supply 114, can have reduced effective vaporization time (i.e., faster evaporation) relative to a deeper pool of the liquid having the same surface area as above because the amount of liquid surface area increases. In other words, a deeper pool of liquid may have evaporation from only the top surface of the pool, but the collective surface areas of the rock pores can be greater than the surface area of the pool even when the same amount of liquid is being stored in either case. For these reasons, the rock supply 114 can be designed and customized for the system 100 in which it is being used and for the fluids with which it is used, wherein a rock supply having greater surface area (e.g., more numerous/smaller stones or more pores) can be used when evaporation rates are desired to be high, and a rock supply having less surface area (e.g., fewer/larger stones or fewer pores) can be used when evaporation rates are desired to be low.

Figure 2:
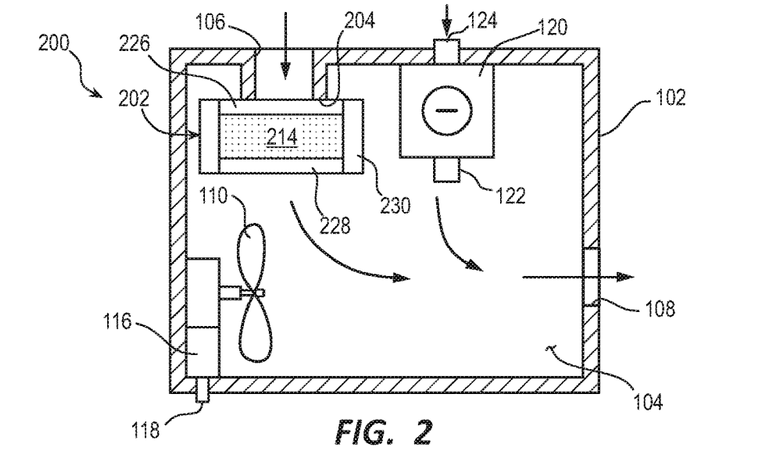
FIG. 2 is a side section view diagram of another diffuser system of the present disclosure.

FIG. 2 illustrates another embodiment of the system 200 similar to system 100 of FIG. 1. Various components of the system 200 serve a similar function as components in system 100, and these components are referenced with the same numerals as in FIG. 1 to avoid repetition. In this system 200, the receptacle 112 is not shown (but could be added), and a filter assembly 202 is positioned at the first opening 106. The filter assembly 202 can be gas-permeable so that air can pass through the filter assembly 202 into the internal chamber 104. In some embodiments, the first opening 106 can comprise an internal edge or lip 204 configured to contact the filter assembly 202. The contact between the lip 204 and the filter assembly 202 can limit or eliminate any airflow from passing between the filter assembly 202 and the lip 204, thereby ensuring that substantially all airflow must pass through the filter assembly 202 before entering the internal chamber 104. Thus, the filter assembly 202 can be positioned within a fluid flow path through the housing 102. Airflow passing through the first opening 106 into the internal chamber 104 can be driven by the air mover 110 and can exit the internal chamber 104 via the second opening 108. Thus, the filter assembly 202 can be positioned between the inlet of the housing 102 and the air mover 110 or the outlet of the housing. A negative ion generator 120 can receive air from the internal chamber 104 or via an inlet (e.g., tube 124) that draws in air external to the housing 102. The negative ion generator 120 can emit negative ions into the air stream within the internal chamber 104, and those negative ions can pass through the second opening 108 and the atmosphere around the system 200. In some embodiments, the outlet 122 can open into the internal chamber 104, or the outlet 122 can open external to the housing 102.

The filter assembly 202 can include a plurality of layers of filter material (e.g., 226, 228), a housing 230, and a rock supply 214. Thus, the filter assembly 202 can be used to filter out particles and contaminants from the air that enters the housing 102 through the first opening 106. Additionally, the filter assembly 202 can use its rock supply 214 to retain fluids that are applied to the filter assembly 202. As air passes through the filter assembly 202, such as in the downward direction indicated in FIG. 2, that the air can be imbued with droplets and evaporated fluid from the fluid coating or held by the rock supply 214 to disperse the fluid as it exits the second opening 108. In this fashion, the filter assembly 202 can be referred to as filtering an inlet of the system 200, and negative ions can be added to the droplets as the stream of fluid-imbued air exits the system 200.

Figure 3:
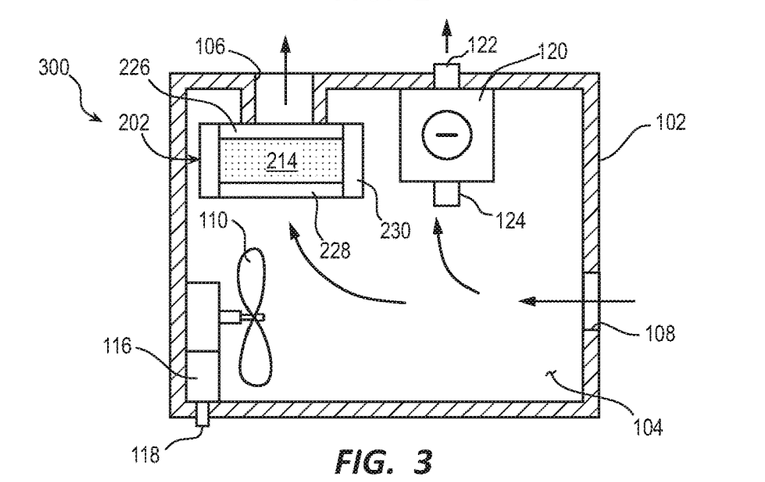
FIG. 3 is a side section view diagram of another diffuser system of the present disclosure.
Figure 4:
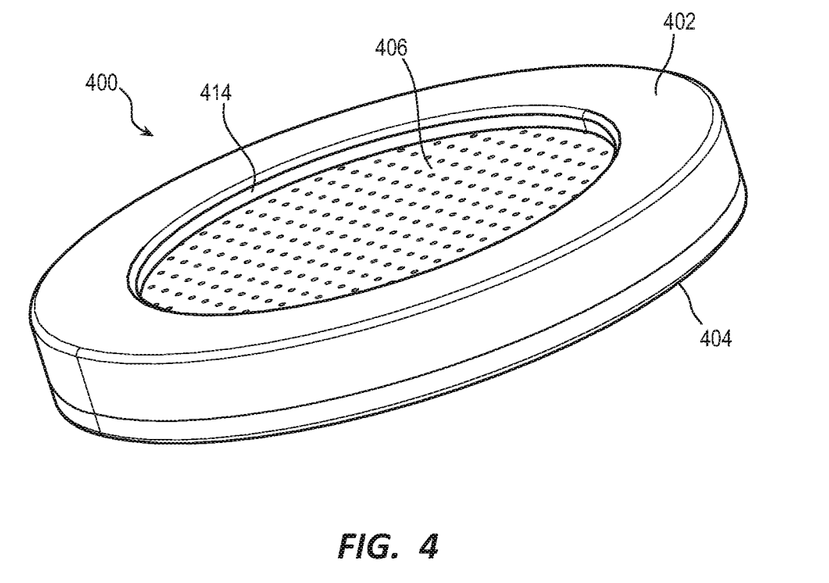
FIG. 4 is a perspective view of a filter assembly of the present disclosure showing side and top surfaces.

FIG. 3 illustrates another embodiment of a system 300 similar to systems 100 and 200 of FIGS. 1 and 2. Various components of the system 300 serve a similar function as components in systems 100 and 200, and these components are referenced with the same numerals as in FIGS. 1 and 2 to avoid repetition. In this system 300, the direction of airflow is reversed as compared to FIG. 2, wherein airflow enters the housing 102 from the second opening 108, enters the filter assembly 202 and the negative ion generator 120 from within the internal chamber 104, passes through the filter assembly 202 to exit through the first opening 106, and passes through the negative ion generator 120 by outlet 122. Thus, in this case, the filter assembly 202 can be referred to as filtering an outlet of the system 300, and negative ions can be added to the atmosphere surrounding the system 300 rather than being added directly to an airstream that has previously passed through the filter assembly 202. In some variations of this embodiment, negative ions can be emitted from the negative ion generator 120 into the internal chamber 104.

FIGS. 4-7 illustrate various views of a filter assembly 400 according to an embodiment of the present disclosure. FIG.

Figure 5:
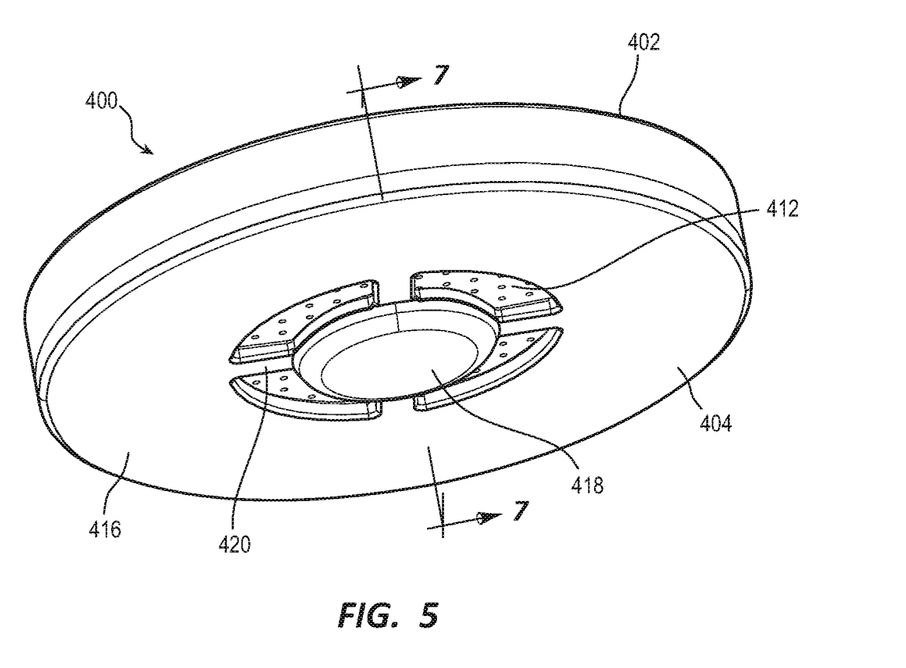
FIG. 5 is a perspective view of a filter assembly of the present disclosure showing side and bottom surfaces.
Figure 6:
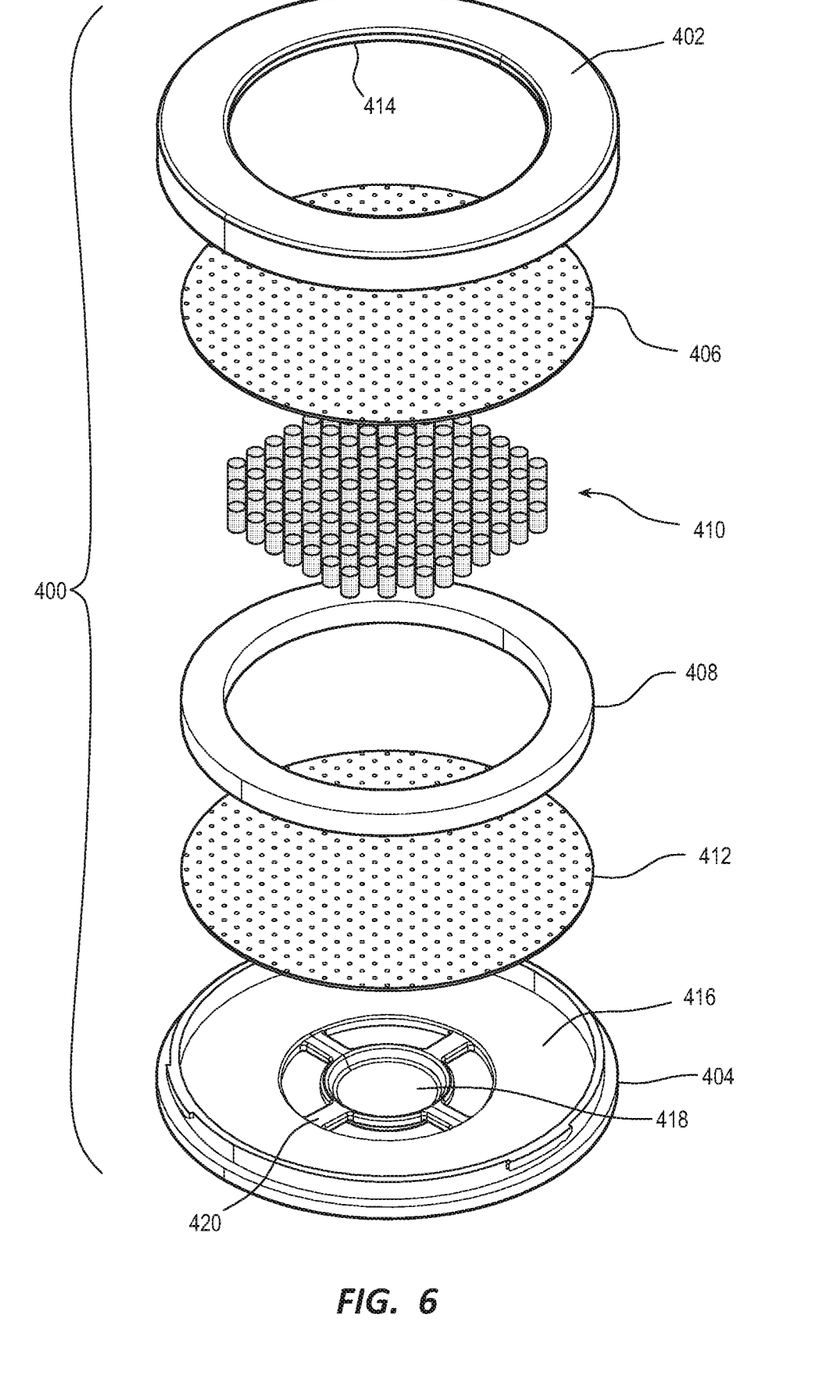
FIG. 6 is an exploded view of the filter assembly of FIGS. 4-5.
Figure 7:
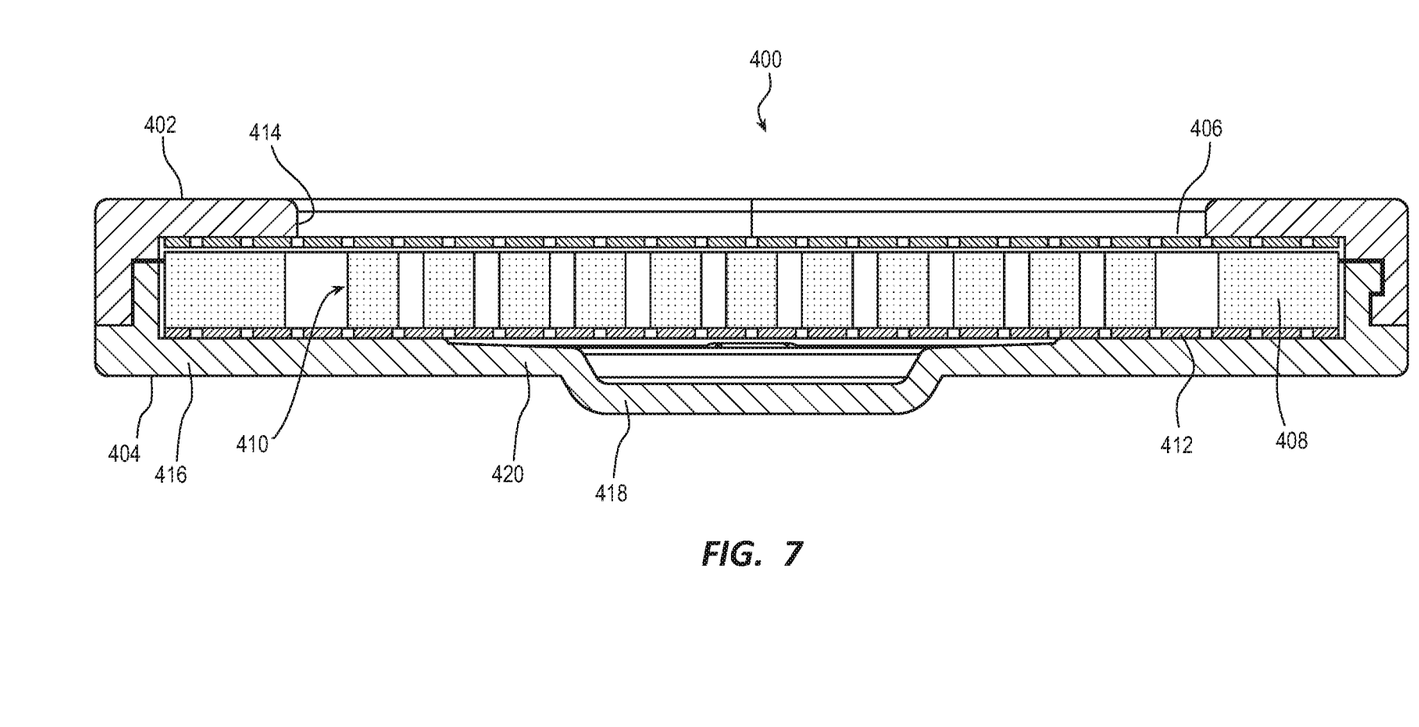
FIG. 7 is a side section view of the filter assembly of FIGS. 4-6 as taken through section lines 7-7 in FIG. 5.

4 shows a perspective top view of the assembled filter assembly 400, FIG. 5 shows a perspective bottom view thereof, FIG. 6 shows an exploded view, and FIG. 7 shows a central side section view, as taken through section lines 7-7 in FIG. 5. The filter assembly 400 can be used in connection with the systems 200, 300 described in FIGS. 2 and 3, wherein the filter assembly 400 can be used as the filter assembly 202 described therein. The filter assembly 400 can include a first outer shell 402 and a second outer shell 404 that define an internal space within which a set of internal components can be retained. In some embodiments, the first and second outer shells 402, 404 can clamp the internal components together when assembled (i.e., vertically-oriented clamping forces are applied to the internal components by the outer shells 402, 404). As shown in FIG. 6, the internal components of the filter assembly 400 can include a first filter layer 406 (i.e., a first retainer layer), a support wall 408 (i.e., a binder) containing a rock supply 410, and a second filter layer 412 (i.e., a second retainer layer). In some embodiments, the first filter layer 406 is omitted. Airflow can be configured to pass through the filter assembly 400 along a gravitational direction (e.g., the downward direction in FIGS. 7-8), and fluid can be applied to the filter assembly 400 parallel to the gravitational direction. The orientation shown in FIGS. 7 and 8 can therefore be referred to as an upright operational position of the filter assembly 400.

The first outer shell 402 can be mounted to the second outer shell 404 to hold the internal components of the filter assembly 400 together as a single unit. The first and second outer shells 402, 404 can comprise a substantially rigid material, such as, for example, a plastic, rigid composite (e.g., fiberglass), or metal material. In this manner, the filter assembly 400 can be substantially rigid and disk-like for easy movement and storage of the filter assembly 400. Generally, the first and second outer shells 402, 404 can be permanently and irreversibly mounted to each other to keep the internal components of the filter assembly 400 secured in place (i.e., to prevent the rock supply 410 from being scattered outside the filter assembly 400). Optionally, in some embodiments, the first and second outer shells 402, 404 can be reversibly removable from each other, such as by twisting or turning one shell relative to the other, so that the internal components can be removed and replaced if needed. Although a generally circular configuration is shown in FIGS. 4 through 7, the top profile shape of the filter assembly 400 can take on a variety of other shapes, such as, for example, an elliptical shape, a square shape, rectangular shape, etc. Thus, the outer shells 402, 404 and the internal components can be adapted to have different, non-circular shapes to fit the overall shape of the filter assembly 400.

The first outer shell 402 can include a wide top opening 414 that allows access to and exposes the top surface of the first filter layer 406 when the filter assembly 400 is assembled. The wide top opening 414 can be configured as the inlet side of the filter assembly 400, wherein fluids are configured to be deposited into the filter assembly 400 through the top opening 414. Thus, fluids can be deposited onto the first filter layer 406 through the top opening 414. Those fluids can pass through the first filter layer 406, either through a one or more small apertures in the first filter layer 406 or by seeping through fibers or spongy material in the first filter layer 406. After passing through the first filter layer 406, the fluids can permeate and coat the rock supply 410 directly beneath the first filter layer 406, as indicated in FIGS. 6 and 7.

Any excess fluid that passes through the rock supply 410 can come into contact with the second filter layer 412, and any fluid that passes through the second filter layer 412 can pass into contact with the second outer shell 404. For example, fluid that passes through the second filter layer 412 near the outer circumference thereof can pass onto a collecting plate portion 416 of the second outer shell 404. Fluid that passes through the second filter layer 412 near the center thereof can pass on to a cup, reservoir, or tank 418 in the center of the second outer shell 404 underneath the rock supply 410 and second filter layer 412. The tank 418 can be connected to the second outer shell 404 by a set of radial bars 420. The radial bars 420 can also allow fluid on the collecting plate portion 416 to flow into the tank 418. As shown in FIG. 7, the radial bars 420 can have a sloped top surface that allows the fluid to flow naturally into the tank 418 in a funnel-like manner. Accordingly, the top surfaces of the radial bars 420 can act as a funnel that guides drops of liquid into the tank 418. The tank 418 can retain fluid due to its cup shape while the filter assembly 400 is oriented with the top opening 414 facing upward. Any fluid within the tank 418 can evaporate over time as air flows past it and beyond the filter assembly 400 (e.g., through the openings between the bars 420), or it can collect in the tank 418 until a user removes the filter assembly 400 to pour it out.

The first filter layer 406 and the second filter layer 412 can comprise a thin filtering material (e.g., cotton, spun fiberglass, paper, cloth, or other fibrous material) configured to collect particles, dirt, and other contaminants that pass through the top opening 414 or through the rock supply 410. The filter layers 406, 412 can have a sufficiently rigid construction to prevent them from sagging within the outer shells 402, 404 due to the weight of the rock supply 410 or fluids applied to the filter assembly 400. The second outer shell 404 can also provide support to the internal components to limit or prevent sagging. The filter layers 406, 412 can be beneficially removable and replaceable from the filter assembly 400 so that they can be cleaned or switched out when they are soiled or clogged. In some embodiments, the filter layers 406, 412 can comprise anti-bacterial or anti-mildew materials or construction, wherein the materials or material properties limit reproduction or accumulation of bacteria on their surfaces. For instance, anti-bacterial properties can be granted by increasing the fiber size of fibers in the filter layers, by using polymer- or metal-infused coatings on the filter layers (e.g., copper, titanium, and related alloys), or by using by using intrinsic polymer- or metal-infused materials in the filter layers.

The support wall 408 can provide spacing between the filter layers 406, 412 so that an internal void is formed for positioning the rock supply 410. The support wall 408 can also help limit the amount of radial spreading of the rock supply 410 so that the rock supply remains substantially centered in the filter assembly 400. By keeping the rock supply 410 centered within the filter assembly 400, fluids can be applied to the center of the first filter layer 406, and portions of the outer shell 402 radially surrounding the top opening 414 will not block fluid from dropping onto the rock supply 410. Thus, the support wall 408 can reduce the amount of rock supply material needed between the filter layers 406, 412. Additionally, the support wall 408 can act as a spacer between the filter layers 406, 412 that can be clamped against when the outer shells 402, 404 are assembled, thereby limiting the amount of movement possible for the internal components of the filter assembly 400. For example, in some embodiments, if the support wall 408 were removed, the rock supply 410 could distribute itself more unevenly between the filter layers 406, 412, thereby potentially leading to the space between the filter layers 406, 412 collapsing and preventing rock supply material from occupying an even and consistent amount of height between the filter layers 406, 412. By keeping the distance between the filter layers 406, 412 roughly consistent, the amount of rock supply material between the layers can remain more evenly distributed, thereby leading to better, more even saturation of fluids across the rock supply 410 which, in turn, leads to more even evaporation and diffusion of the fluids in airflow passing through the filter assembly 400.

In some embodiments, the support wall 408 can bind together the first and second filter layers 406, 412 at their outer perimeters/diameters, thereby enabling the outer shells 402, 404 to be removed without causing the internal components to separate from each other. Additionally, in some embodiments where the support wall 408 attaches the first and second filter layers 406, 412 to each other, the outer shells 402, 404 can be omitted entirely or can be integrally formed as part of another housing (e.g., 102). The support wall 408 can therefore be adhered to the inner surfaces of the filter layers 406, 412 that are configured to face the rock supply 410. In some cases, however, the first filter layer 406 is adhered or otherwise attached to the inner surface (i.e., the downward-facing surface) of the upper outer shell 402, and the second filter layer 412 is adhered or otherwise attached to the inner surface (i.e., the upward-facing surface) of the lower outer shell 404.

The rock supply 410 can comprise aggregate pebbles, chunks, balls, powder, or dust made from volcanic rock or other vesicular rock (e.g., pitted rock with many cavities/vesicles at least on its surface). For example, the volcanic rock can comprise basalt, pumice, pumicite, scoria, andesite, or other aphanitic, igneous rocks. The rock supply 410 can be a natural fluid collector and retainer due to the fluid flowing or being drawn into the cavities in the rock (e.g., via surface tension, adhesive forces, wicking, and/or capillary action). The fluid held by the cavities can have reduced surface area for evaporation (relative to a simple droplet or a puddle of the fluid on a flat surface) due to the cavity walls preventing evaporation and fluid flow in some directions.

The rock supply 410 can be distributed between the filter layers 406, 412 in a substantially single layer of stones (or a single stone). In other words, the vertical thickness of the collective rock supply (as defined along the central vertical axis of the filter assembly 400 in FIG. 7) can be substantially equal to the average vertical thickness of the individual stones within the rock supply 410. In some embodiments, the layer of rock material can comprise stones that at least partially overlap with each other or that form a group of layers that collectively fill a substantial portion of the space defined within the support wall 408. Accordingly, aggregate rock material can comprise a first portion that overlaps a second portion thereof, when viewed along an axis extending through a vertical dimension (e.g., the thinnest/vertical dimension in FIG. 7) of the rock supply 410 as a whole (or the filter assembly 400 as a whole). For example, some stones in the rock supply 410 can vertically overlap other stones, such as when there are two or more overlapping layers of stones in the rock supply 410. In some embodiments, the rock supply 410 can comprise a layer of powder or sand-like grains of material distributed between the filter layers 406, 412.

Figure 8:
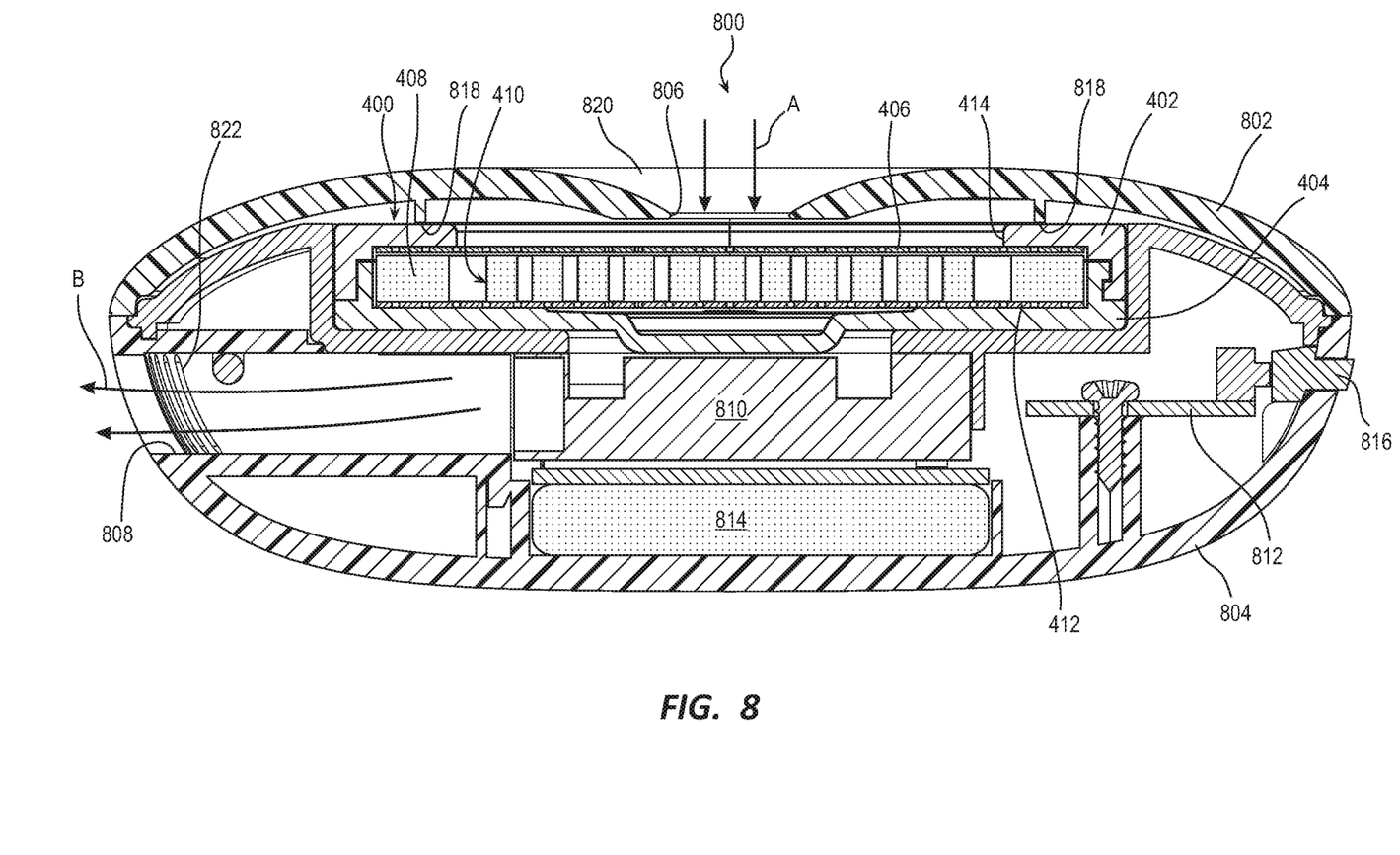
FIG. 8 is a side section view of a diffuser system of another embodiment of the present disclosure.

FIG. 8 illustrates a side section view of a diffuser system 800 according to an example embodiment of the present disclosure. The diffuser system 800 can contain a filter assembly 400. The diffuser system 800 comprises a housing having an upper housing shell 802 and a lower housing shell 804. The upper housing shell 802 can comprise a first opening 806 used as an inlet opening for the diffuser system 800, and the lower housing shell 804 can comprise a second opening 808 configured as an exhaust opening for the system 800. An air mover 810 is positioned within the housing shells 802, 804 and is configured to draw air through the first opening 806, through the filter assembly 400, and out through the second opening 808, as indicated by the arrows A and B in FIG. 8. In a variation on this embodiment, the air mover 810 can be configured to drive air in the opposite directions relative to arrows A and B.

The air mover 810 can be electrically connected to a controller (e.g., printed circuit board 812) and to an electrical power source (e.g., battery 814) to drive a motor or similar feature of the air mover 810. User input such as power on/off control can be provided by an input feature 816 (e.g., button, dial, or switch) that modifies operation of the controller. Accordingly, structures of the diffuser system 800 correspond to (and can be constructed and function similar to) the components of system 200 of FIG. 2 or system 300 of FIG. 3.

As shown in FIG. 8, the filter assembly 800 is configured to engage a lip 818 extending around the inside of the upper housing shell 802 and surrounding the first opening 806. Air drawn through the first opening 806 is therefore forced through the filter assembly 400 in order to exit the housing shell (thereby filtering the air and infusing it with fluid droplets) rather than being able to bypass the filter assembly 400. The top surface 820 of the upper housing shell 802 can comprise a central sloped area that can funnel fluids through the first opening 806 and directly and centrally onto the filter assembly 400. The top surface 820 can therefore be referred to as a funnel surface or funnel slope surrounding the first opening 806.

Additionally, FIG. 8 shows an embodiment wherein the second opening 808 comprises a plurality of slots 822 that permit airflow out of the lower housing shell 804. Those slots 822 can simultaneously prevent large objects from passing into the lower housing shell 804, thereby protecting the air mover 810 from objects that could interfere with its operation. The slots 822 can be large enough to permit typically-sized fluid droplets to pass through, and can, in some embodiments, be small enough to limit and filter out passage of large droplets carried by the exhaust airflow.

Figure 9:
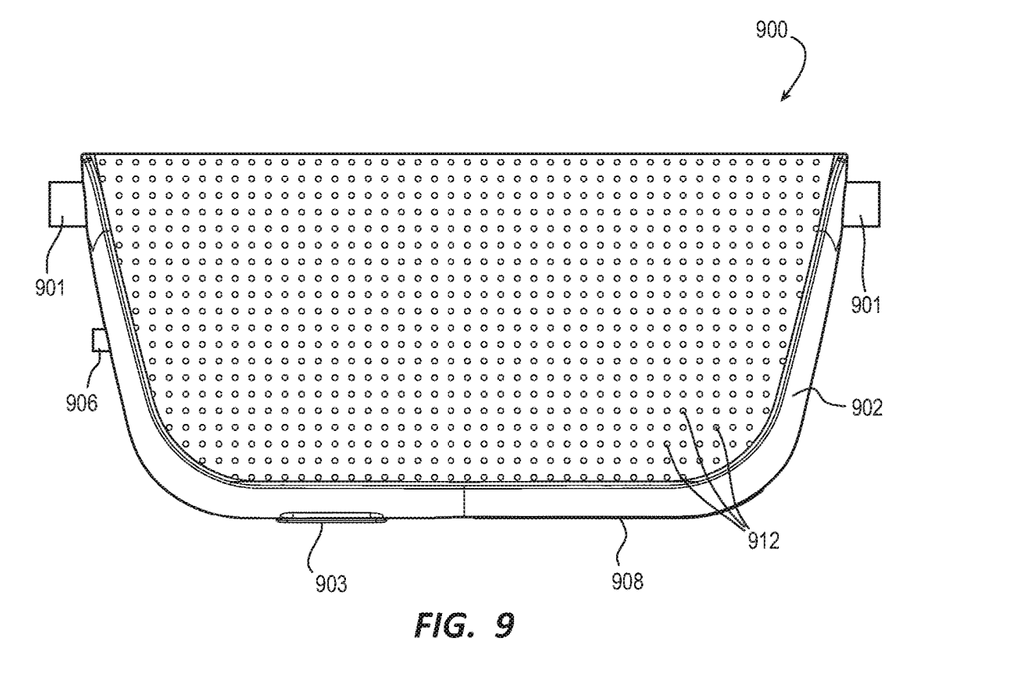
FIG. 9 is a side view of a diffuser system of another embodiment of the present disclosure.
Figure 10:
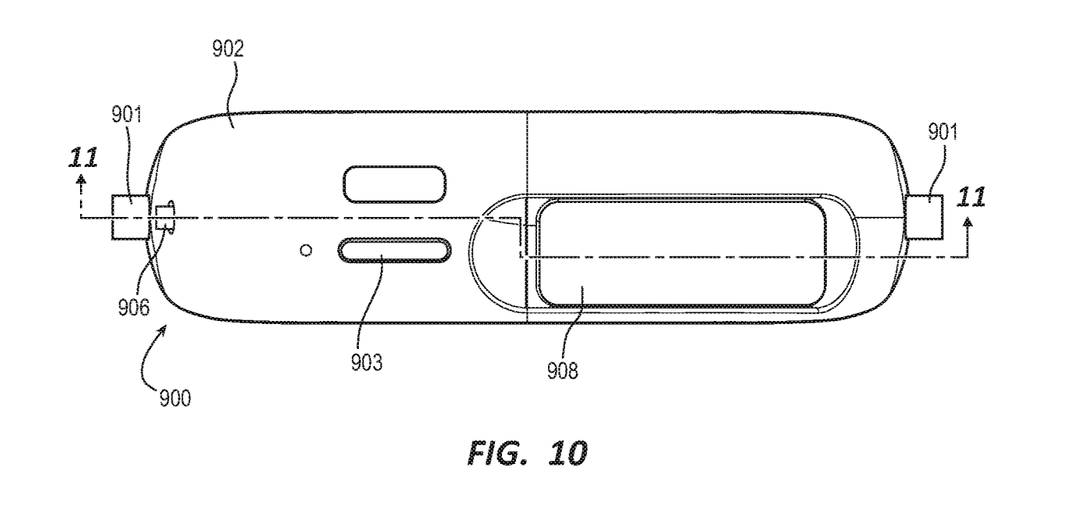
FIG. 10 is a bottom view of the diffuser system of FIG. 9.
Figure 11:
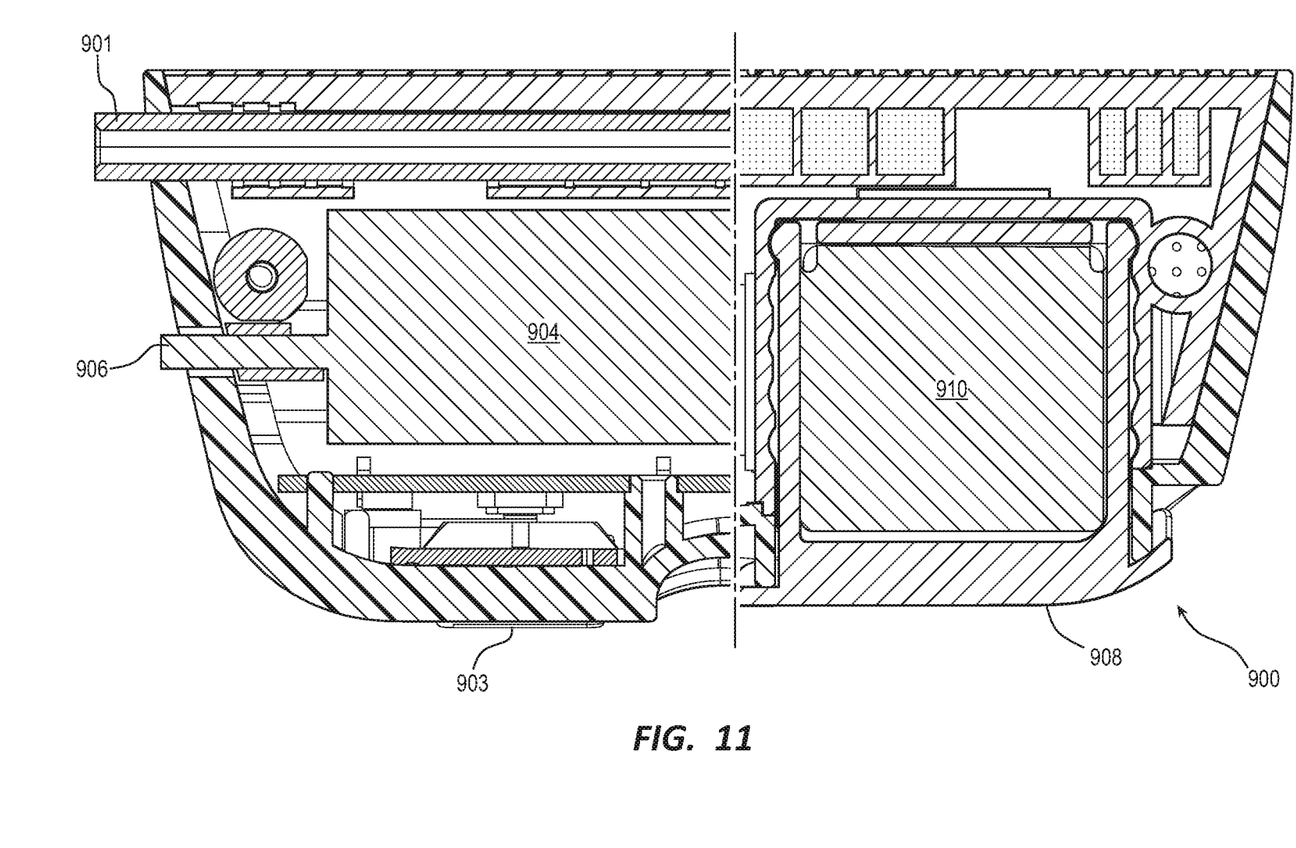
FIG. 11 is a side section view of the diffuser system of FIGS. 9-10 as taken through section lines 11-11 in FIG. 10.

FIGS. 9 and 10 illustrate an alternate embodiment of a diffuser system 900. FIG. 11 shows a section view of the diffuser system 900 as taken through section lines 11-11 in FIG. 10. The diffuser system 900 is configured as a wearable device, such as a device worn around a neck of a user, and the system 900 can alternatively be used as a standalone, non-worn (e.g., tabletop) device. To facilitate wearing the system 900, a string or neckband can be attached to or threaded through a tube 901 in the upper end of the housing 902.

The housing 902 can contain a negative ion generator 904 (see FIG. 11) with an outlet 906 configured to emit negative ions external to the housing 902. The negative ion generator 904 comprises features described above in connection with other negative ion generators described herein. A controller, power supply, and user control input device (e.g., button 903) can be provided in the housing 902 to power and control the negative ion generator 904 as well.

The housing 902 can be configured to retain a receptacle 908 (i.e., a tray, bin, cup, or similar rock reservoir) that holds a rock supply 910 (see FIG. 11) within the housing 902. The rock supply 910 can comprise features and materials described above in connection with other rock supplies described herein. The housing 902 can comprise a perforated outer surface having a plurality of apertures 912 through which airflow can penetrate. The airflow is in fluid communication with the rock supply 910, so fluids located on or absorbed by the rock supply 910 can evaporate or diffuse into air that enters the apertures 912 and can subsequently pass back out of the housing 902 through the apertures 912. The receptacle 908 can be removable from the housing 902 in a drawer-like manner, wherein a user can grasp the receptacle 908 and pull it out to reveal and expose the rock supply 910 stored in the housing 902. With the rock supply 910 exposed, a user can apply fluid to the rock supply 910, remove/replace/adjust the rock supply 910, or perform other actions.

The diffuser system 900 is similar in function to system 100 since the rock supply 910 is positioned within an internal cavity of housing 902 and within a receptacle 908 similar to receptacle 112. The negative ion generator 904 is also positioned in the housing 902 and emits ions external to the housing 902, similar to generator 120. The diffuser system 900 can further comprise an air mover (similar to air mover 110), but the embodiment shown in FIGS. 9-11 uses natural air flow diffusion (e.g., airflow generated by the movement of the wearer of the device) to drive air through the apertures 912 (which correspond in function to the first and second openings 106, 108).

Various inventions have been described herein with reference to certain specific embodiments and examples. However, they will be recognized by those skilled in the art that many variations are possible without departing from the scope and spirit of the inventions disclosed herein, in that those inventions set forth in the claims below are intended to cover all variations and modifications of the inventions disclosed without departing from the spirit of the inventions. The terms "including:" and "having" come as used in the specification and claims shall have the same meaning as the term "comprising."

What is claimed is:

1. A lava rock fluid diffuser, comprising:
   a housing defining an air inlet in a top wall of the housing and an air outlet;
   a fluid flow path extending at least partially downward along a gravitational direction from the air inlet to the air outlet of the housing;
   a lava rock material positioned in the housing, the lava rock material having a recessed surface configured to retain a fluid;
   wherein
   evaporation of the fluid from the lava rock material moves the fluid into the fluid flow path to exit the outlet of the housing;
   the lava rock material is positioned within a filter; and
   the filter comprises a shell having a fluid reservoir, and the fluid reservoir is positioned underneath the lava rock material.

2. The lava rock fluid diffuser of claim 1, wherein the fluid flow path changes directions between the air inlet and the air outlet.

3. The lava rock fluid diffuser of claim 1, further comprising a negative ion generator positioned in the housing and configured to emit negative ions into the fluid flow path.

4. The lava rock fluid diffuser of claim 1, wherein the lava rock material is further positioned on a tray, the tray being removable from the housing through a side surface of the housing.

5. The lava rock fluid diffuser of claim 1, further comprising a receptacle disposed in the housing, the lava rock material being further positioned in the receptacle, the receptacle defining a single open side through which evaporation of the fluid from the lava rock material moves into the fluid flow path to exit the outlet of the housing.

6. The lava rock fluid diffuser of claim 5, wherein the fluid flow path is directed across the single open side of the receptacle.

7. The lava rock fluid diffuser of claim 1, wherein the shell further having a fluid connecting plate portion, the fluid connection plate portion is connected to the fluid reservoir via radial bars having openings between adjacent each other; and the radial bars are configured to allow fluid on the fluid connecting plate portion to flow into the fluid reservoir.

8. The lava rock fluid diffuser of claim 7, wherein the filter comprises:
   a first filter layer having a first fluid-penetrable material;
   a porous volcanic rock layer made of the lava rock material and adjacent to the first filter layer;
   a second filter layer having a second fluid-penetrable material adjacent to the volcanic rock layer; and
   a binder coupling the first filter layer, the porous volcanic rock layer, and the second layer in a layered orientation around a perimeter of the porous volcanic rock layer.

9. The lava rock fluid diffuser of claim 1, wherein the filter engages a lip extending around an inside of the top wall of the housing and surrounding the air inlet.

10. The lava rock fluid diffuser of claim 8, wherein the porous volcanic rock layer comprises an aggregate of porous volcanic rock particles.

11. The lava rock fluid diffuser of claim 10, wherein a first portion of the aggregate overlaps a second portion of the aggregate along an axis extending through a vertical dimension of the filter.

12. The lava rock fluid diffuser of claim 8, wherein the first fluid-penetrable material and the second fluid-penetrable material comprise anti-bacterial materials.

13. The lava rock fluid diffuser of claim 8, wherein the binder is configured to clamp the first filter layer and the second filter layer toward each other.

14. The lava rock fluid diffuser of claim 8, wherein the binder is adhered to the perimeter of the porous volcanic rock layer.

15. The lava rock fluid diffuser of claim 1, wherein the housing comprises a funnel surface surrounding the air inlet, the funnel surface comprising a bottom opening directed toward the filter.

16. The lava rock fluid diffuser of claim 1, wherein airflow is configured to enter the air inlet along a first direction and configured to exit the air outlet along a second direction, the first direction being perpendicular to the second direction.

* * * * *